United States Patent [19]

Peters

[11] Patent Number: 4,844,056

[45] Date of Patent: Jul. 4, 1989

[54] TRACTION DEVICE AND METHOD FOR RELOCATING DISLOCATED SHOULDERS

[76] Inventor: Robert M. Peters, P.O. Box 323, Jackson, Wyo. 83001

[21] Appl. No.: 90,948

[22] Filed: Aug. 28, 1987

[51] Int. Cl.$^4$ ................................................ A61F 5/04
[52] U.S. Cl. .................................. 128/77; 128/24 R; 128/94
[58] Field of Search .................. 128/78, 24 R, 44, 94, 128/133, 134, 77

[56] References Cited

U.S. PATENT DOCUMENTS

| | | | |
|---|---|---|---|
| 2,652,050 | 9/1953 | Schoeller | 128/94 |
| 3,698,389 | 10/1972 | Guedel | 128/77 |
| 3,888,244 | 6/1975 | Lebold | 128/77 |
| 4,132,229 | 1/1979 | Morrison | 128/134 |
| 4,232,664 | 11/1980 | Blatt | 128/94 |
| 4,489,216 | 12/1984 | Blackwood et al. | 128/77 |
| 4,573,482 | 3/1986 | Williams, Jr. | 128/133 |
| 4,660,550 | 4/1987 | Bodine | 128/88 |
| 4,699,129 | 10/1987 | Haserude et al. | 128/80 C |
| 4,709,693 | 12/1987 | Key | 128/80 G |

Primary Examiner—Edgar S. Burr
Assistant Examiner—Tonya Lamb
Attorney, Agent, or Firm—Andrew D. Maslow

[57] ABSTRACT

A device is provided for use by a physician to relocate a dislocated shoulder of a patient. The device includes a bent rigid member, an upper arm connecting member attached to one end of the bent rigid member, a lower arm connecting member attached to the other end of the bent rigid member, a loop attached to the bent rigid member. The device is also supplied with belt means for attaching the loop to the physician in order to allow him to apply force to the bent rigid member by using his body weight.

12 Claims, 4 Drawing Sheets

TRACTION DEVICE AND METHOD FOR RELOCATING DISLOCATED SHOULDERS

BACKGROUND OF THE INVENTION

1. Field of the Invention

This invention relates generally to orthopedic devices and particularly to a device for aiding a physician in the reduction of a dislocated shoulder.

2. Description of the Prior Art

Anterior dislocations of the shoulder are the most common dislocations of a major joint. Many different techniques have been described to attain reduction. Among those known are the Hippocratic, simple traction, traction counteraction, traction with lateral traction, Stimson technique, Milch technique, the Kocher maneuver or modification thereof.

An external rotation method has been reported and evaluated in a paper entitled, "Closed Reduction of Anterior Subcoracoid Shoulder Dislocation", *Orthopedic Review*, Volume XV, No. 5, May 1986. A modified Kocher maneuver has been reported by Snell et al in *Orthopedics*, November 1983, Volume 6, No. 11 at page 1439. Another technique is reported by Waldion in *Orthopedic Review*, Volume XI, No. 4, April 1982 at page 105.

The Hippocratic technique requires an assistant, is brutal to already contused shoulder tissues, is uncomfortable to the patient and frequently fails in muscular individuals. The Kocher leverage technique may injure the capsule and axillary structures and uniformly fails in obese individuals. The Stimson technique requires shifting an already uncomfortable patient to the prone position, elevating the patient sufficiently to allow application of weights to the forearm and repositioning the patient for x-ray.

The above methods are fairly crude and do not give the physician a great deal of control over the direction of the pressures being applied to relocate the shoulder.

U.S. Pat. No. 4 610,244 shows a brace for restraining a shoulder including a sling-like member which is adapted to be secured or around the waist of the person having the injured shoulder and includes a pair of straps attached to both the forearm and the upper arm using suitable closures.

U.S. Pat. No. 4 572,172 is directed to a cast system including a 90 degree shaped cast member having a sling attached thereto. The sling goes around the head and neck of the injured person rather than a physician attempting to put pressure on the injured area. United States Pat. No. 4,232,664 shows another similar arm sling.

U.S. Pat. No. 3,698,389 is directed to an elbow locking device including an upper and lower arm shell connected through a bendable slide which, when secure, holds the elbow in place.

None of the above patents are directed to enabling a physician to use his body weight to relocate a dislocated shoulder nor do they suggest the same.

SUMMARY OF THE INVENTION

It is an object of the present invention to provide a device for allowing a physician to directly apply his weight to the affected arm of a patient having a dislocated shoulder.

It is another object of the present invention to provide a device which enables a physician to apply traction to a patient's arm directly in line with the humerus.

Yet another object of the present invention is to provide a device for applying in line traction to an arm of a patient having a dislocated shoulder. The traction is applied at one pivot point, namely at the elbow, thereby allowing rotation of the humerus of approximately 180 degrees.

Another object of the invention is to allow the physician to either abduct or adduct the shoulder joint by moving his body position.

Still another object of the invention is to provide a device which allows a physician to have greater control over the traction pressures being applied to relocate a shoulder.

A still further object of the invention is to provide a device which allows a physician to regulate the pressure being applied to the arm of a patient with a dislocated shoulder while still having two hands free, one hand to rotate the patient's arm and the other hand to feel the joint activity in the shoulder.

Another object of the invention is to provide for the physician to use his body weight in a controllable manner with little fatigue resulting in an efficient means to control the joint affected.

These and other objects are achieved according to the present invention by providing a device for use by a physician to relocate a dislocated shoulder, the device having a bent rigid member, a lower arm connecting means attached to one end of the bent rigid member and an upper arm connecting means attached to the other end of the bent rigid member. The upper and lower arm connecting means are used to attach the bent member to the patient's arm above and below the elbow so that the bent rigid member is located at the elbow. A strap is attached to the bent rigid member and means for attaching the strap to the physician is provided in order to allow him to apply his body weight to the affected arm while still having free use of his two hands in order that he may rotate the affected arm and feel the dislocated shoulder joint at the same time.

The bent rigid member is adapted to fit on the outside of the patient's elbow and is preferably bent at an angle of about 90 degrees. The upper and lower arm connecting means are preferably made of a flat sheet of flexible material having placed thereon fastening means so that the flat sheet of flexible material can be securely wrapped around the respective upper and lower portions of the arm. The strap is preferably attached to the bent rigid member at the elbow. The upper and lower connecting means are provided with respective sleeves into which the bent rigid member is inserted. When the upper and lower connecting means are fastened to the respective upper and lower portions of the affected arm and a force is exerted on the strap, traction thereby is applied directly in line with the humerus. With the device of the invention on the physician is still able to rotate the humerus about 180 degrees while maintaining traction pressure by exerting a continuous force on the strap. Preferably means are provided to attach the strap directly to the physician. Such means include a belt adapted to go around the waist of the physician. The belt can be placed through a loop formed by the strap or through means for connecting the belt to such strap.

The strap and the belt are preferably made of nylon webbing and the flexible material used for the upper and lower arm connecting means is preferably a nylon cordora or similar type material with Velcro fastening means.

DESCRIPTION OF THE PREFERRED EMBODIMENT

Figure 1:
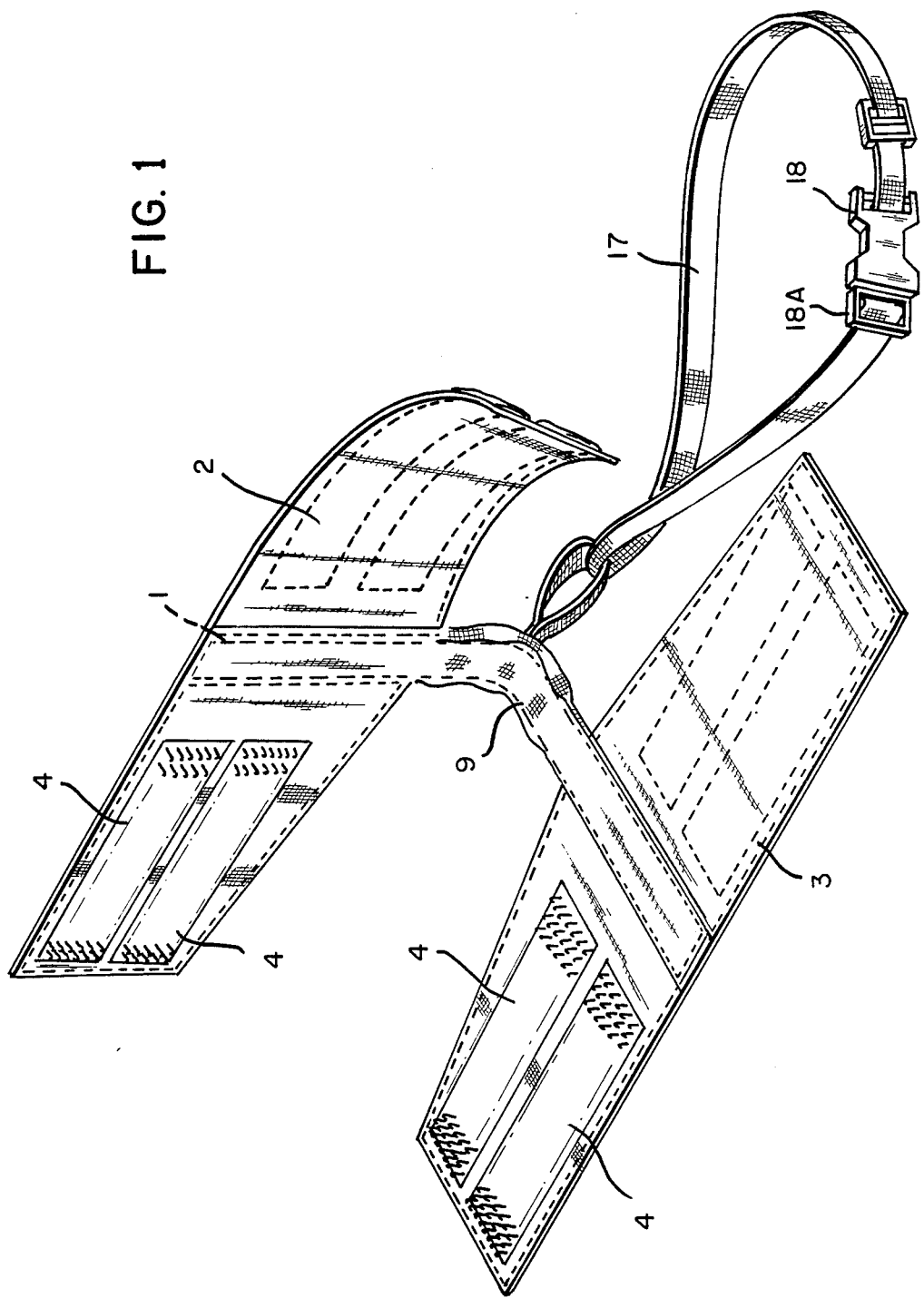
FIG. 1 is a perspective view showing the inside of the arm connecting means.
Figure 2:
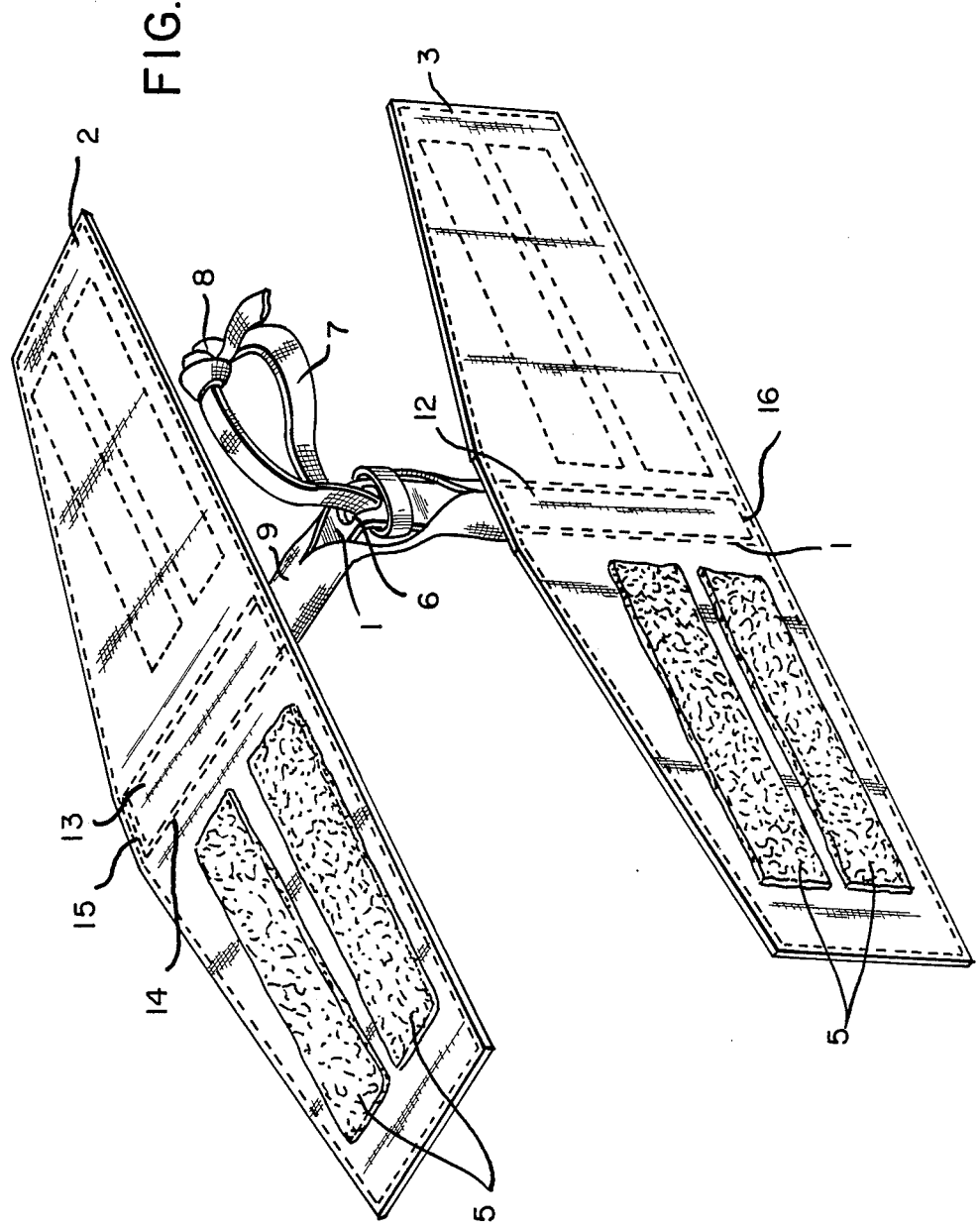
FIG. 2 is a perspective view showing the outside of the arm connecting means and showing another type of belt means for attaching the traction device to a physician.
Figure 3:
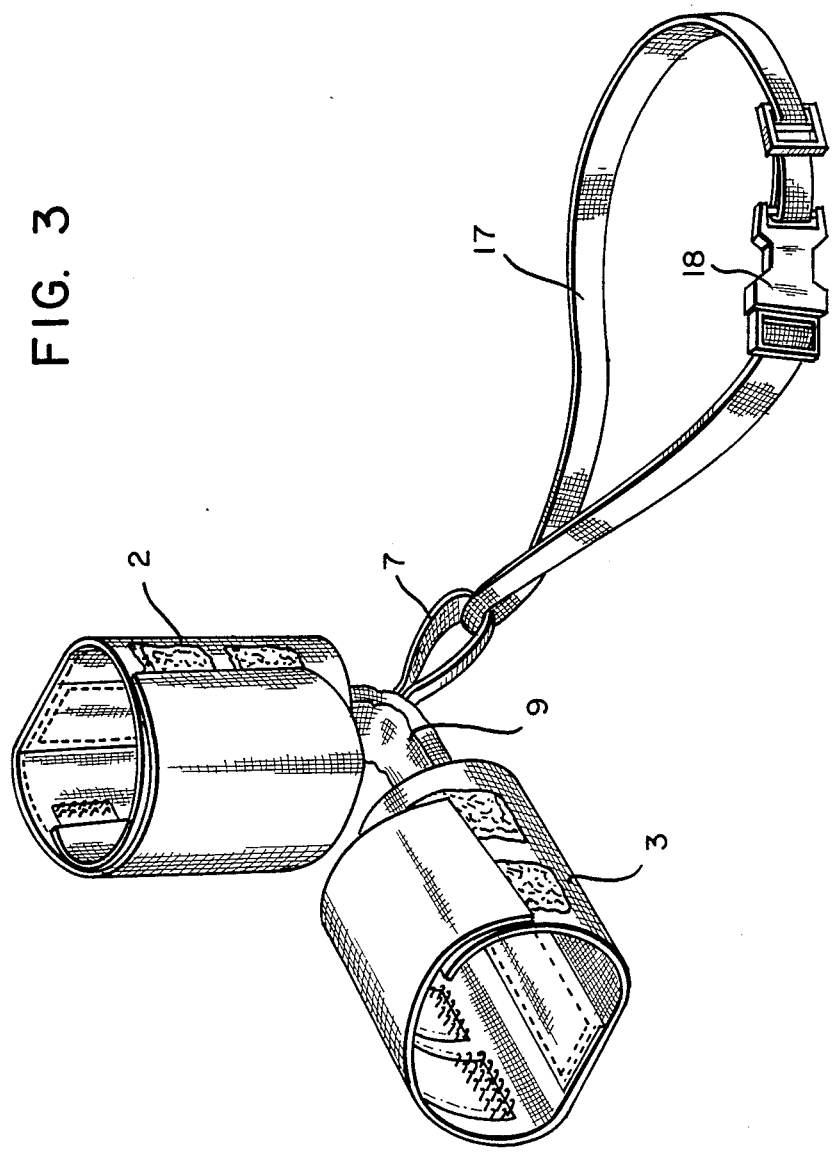
FIG. 3 is a perspective view showing the arm connecting means in a closed position.

Referring now more particularly to FIG. 1 thru FIG. 4 of the drawing, a device for use by a physician to relocate a dislocated shoulder is shown including a bent rigid member 1 attached to upper arm connecting means 2 and lower arm connecting means 3. Upper and lower arm connecting means are made of nylon cordora and are of preferably a width of 1½ to 3 inches and sufficient length to be conveniently wrapped about one and a quarter to one and a half times around the patient's upper and lower arms, similar to the commonly used blood pressure devices. The upper and lower connecting means are supplied with Velcro hooks 4 and loops 5.

The bent rigid member 1 is bent at about 90 degrees and is made of flat stainless steel and is shaped so as to contour the patient's elbow when bent at a 90 degree angle and extending at least about three inches up and down from the center of the elbow. A hole 6 is made at the portion of the bent rigid member adapted to be placed at the elbow. Strap or loop 7 is wrapped around bent rigid member 1 slightly above or below the bend and then both ends of strap 7 are inserted through hole 6 and the ends are tied in a knot 8 thereby fastening strap 7 to the bent rigid member. Strap 7 is preferably one half inch wide nylon webbing. Cover 9 of bent rigid member 1 is sewn to the upper and lower connecting means along seams 11,12,13,14,15 and 16 thereby providing a sleeve for connecting the bent rigid member to the upper and lower arm connecting means. Belt 17 is a two inch wide nylon webbing strap supplied with a quick adjustment fastener with female member 18 and male member 18A, or can be simply tied in a knot so as to fit around a physician's waist, and is inserted through the loop formed by strap 7 and knot 8. This enables the physician to quickly attach belt 17 to strap 7 and adjust it so that the physician during traction is close to the patient.

To operate the device, the physician 20 places the device on the patient's arm with the patient's elbow conforming to the bent rigid member. The upper and lower arm connecting means are securely fastened to the upper and lower portions of the arm with the patient's elbow being held at about a 90 degree angle.

Figure 4:
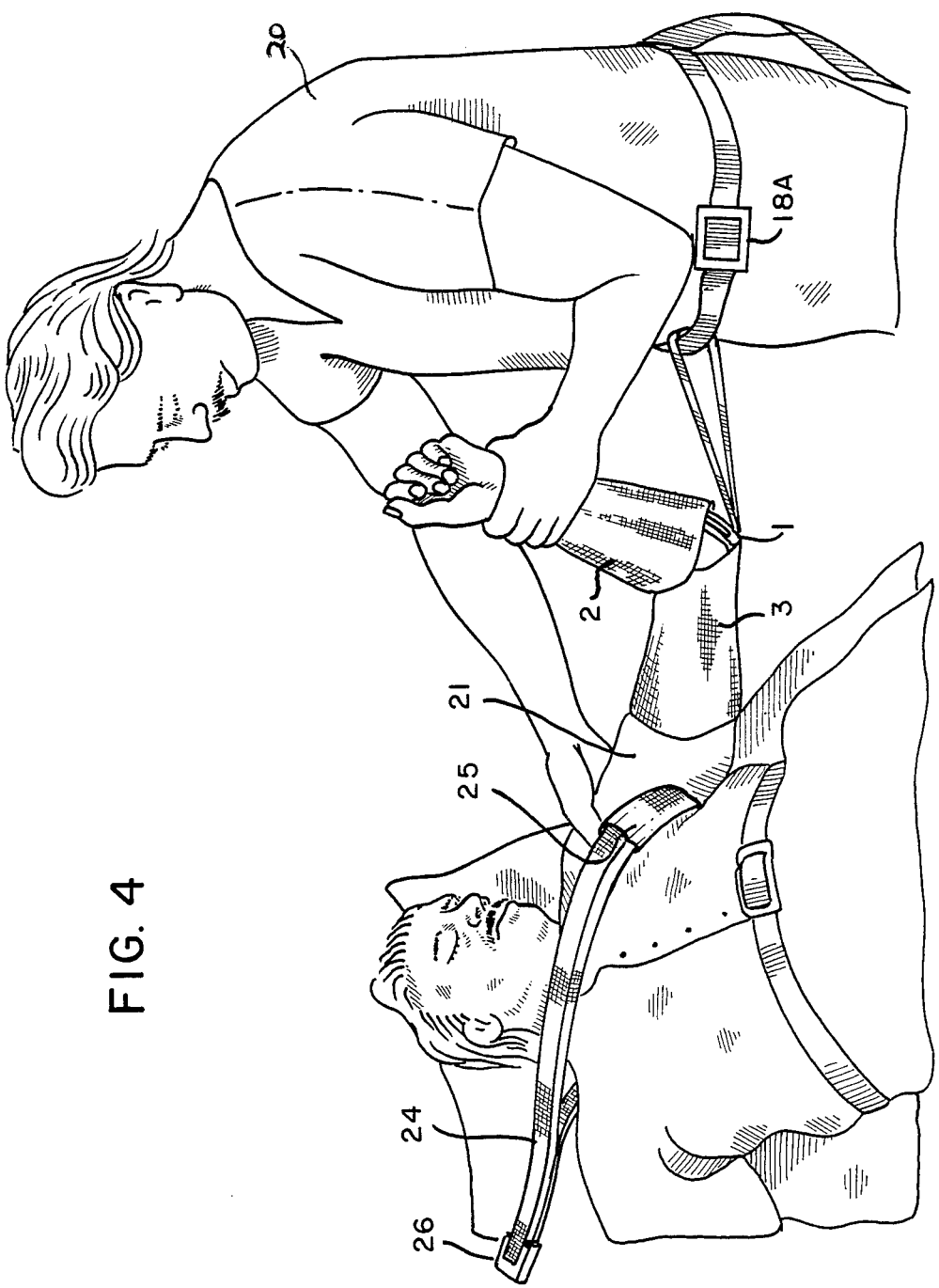
FIG. 4 is a perspective view showing a physician using the traction device on a patient.

As shown in FIG. 4, the patient is placed on a secure horizontal surface such as a bed and is strapped thereto with strap 24 with padding 25 as shown in FIG. 4. Thus Strap 24 is provided with a quick countertraction is applied to the patients shoulder. fastener 26 with a male member and a male member and a female member. The physician, now by leaning away from the patient, will be able to apply his weight directly to the upper arm of the patient while simultaneously being able to place one hand on the patient's shoulder and the other hand on the patient's wrist. Strap 24 is similar to belt 17 but is longer and serves to provide countertraction. Padding 25 is slideably attached to strap 24 and is fit into the axilla of the affected arm. The physician may then rotate the patient's upper arm to about a 180 degree arc having its center at the patient's elbow. Thus, the physician is able to apply pressure to the shoulder joint directly along the line of the humerus while at the same time feeling the shoulder joint and rotating the humerus up to 180 degrees. As can be readily understood from the above description and drawing, a light weight portable device is provided allowing a physician to quickly and accurately relocate a dislocated shoulder.

It is to be understood that the above description of the present invention is capable of various changes, modifications, and adaptations, and such are intended to be included within the meaning and range of equivalence of the following claims.

What is claimed is:

1. A device for use by a physician to relocate a dislocated shoulder of a patient, said device comprising:
   a. bent rigid member,
   b. a flexible upper arm connecting means attached to the bent rigid member,
   c. a flexible lower arm connecting means attached to the bent rigid member,
   d. Means attach the bent rigid member to the physician to allow the physician to apply his body weight to directly pull the bent rigid member.

2. A device according to claim 1 wherein said means for allowing the physician to apply his body weight comprises a loop attached to the bent rigid member and means for attaching said loop to the physician.

3. A device according to claim 2 wherein said bent rigid member is bent at an angle of about 90 degrees.

4. A device according to claim 2 wherein said bent member comprises flat stainless steel.

5. A device according to claim 2 wherein said strap comprises nylon webbing.

6. A device according to claim 2 further comprising countertraction means to secure the patient in a steady position.

7. A device according to claim 6 wherein said countertraction means comprises a strap adapted to secure the patient to a horizontal surface and padding slideably attached to said strap and adapted to fit into the axilla of the arm of the patient's affected shoulder.

8. A device according to claim 2 wherein said means for attaching said strap to the physician comprises an adjustable belt adapted to go around the waist of a physician.

9. A device according to claim 8 wherein said belt and strap comprise nylon webbing and said upper and lower arm connecting means each comprise a sheet of flexible nylon material provided with fastening means to allow the flexible nylon material to be wrapped around and securely fastened to the upper and lower portions of the patient's arm.

10. A device according to claim 2 wherein said upper and lower arm connecting means comprise a flexible material and fastening means on said flexible material to be securely wrapped around the patient's arm.

11. A device according to claim 10 wherein said means for fastening the flexible material comprise Velcro hooks and loops.

12. A method for a physician to relocate a dislocated shoulder of a patient comprising: (1) providing a device comprising:(a) a bent rigid member,(b) a flexible upper arm connecting means attached to the bent rigid member, and (c) a flexible lower arm connecting means attached to the bent rigid member; (2) attaching said device to the patient and to said physician; (3) applying traction to the affected shoulder by the physician using his body weight to pull said device while counter traction 13 applied to hold the patient's shoulder in a relatively fixed position; and (4) rotating the humerus of the arm of the patients affected shoulder 180 degrees while at the same time applying the traction of step 3 directly in line with said humerus.

* * * * *